US009526387B1

(12) United States Patent
Li et al.

(10) Patent No.: US 9,526,387 B1
(45) Date of Patent: Dec. 27, 2016

(54) MITE-REMOVING VACUUM CLEANER

(71) Applicant: EGENPOWER INC., Laguna Niguel, CA (US)

(72) Inventors: Gary Li, Dong Guan (CN); Yao-Hsi Chiu, Taichung (TW)

(73) Assignee: EGENPOWER INC., Laguna Niguel, CA (US)

( * ) Notice: Subject to any disclaimer, the term of this patent is extended or adjusted under 35 U.S.C. 154(b) by 0 days.

(21) Appl. No.: 14/846,245

(22) Filed: Sep. 4, 2015

(51) Int. Cl.
*A47L 7/00* (2006.01)
*A61L 2/10* (2006.01)
*A47L 9/04* (2006.01)
*A47L 9/06* (2006.01)
*A47L 9/00* (2006.01)

(52) U.S. Cl.
CPC ............... *A47L 7/0061* (2013.01); *A47L 7/00* (2013.01); *A47L 7/008* (2013.01); *A47L 9/0483* (2013.01); *A47L 9/0673* (2013.01); *A61L 2/10* (2013.01); *A47L 9/0063* (2013.01)

(58) Field of Classification Search
CPC .......... A47L 7/00; A47L 7/008; A47L 7/0061; A47L 9/0063; A47L 9/0477; A47L 9/0483; A47L 9/0488; A47L 9/0673; A61L 2/10
USPC .................................. 15/328, 339, 379, 382
IPC ........................................ A47L 5/22, 5/25, 7/00
See application file for complete search history.

(56) References Cited

U.S. PATENT DOCUMENTS

| | | | | |
|---|---|---|---|---|
| 8,424,156 | B2* | 4/2013 | Hsu | A47L 5/24 15/339 |
| 2008/0052872 | A1* | 3/2008 | Cho | A47L 5/26 15/421 |
| 2011/0214686 | A1* | 9/2011 | Chavana, Jr. | A47L 9/00 134/1 |
| 2013/0298349 | A1* | 11/2013 | Song | A47L 5/24 15/319 |
| 2014/0182080 | A1* | 7/2014 | Lee | A47L 5/26 15/379 |

FOREIGN PATENT DOCUMENTS

TW   M424153 (U)   3/2012

* cited by examiner

*Primary Examiner* — David Redding
(74) *Attorney, Agent, or Firm* — Muncy, Geissler, Olds & Lowe, P.C.

(57) ABSTRACT

The present disclosure illustrates an mite-removing vacuum cleaner including a cleaner body and a mite-removing device. The mite-removing device is detachably combined with a front section of the cleaner body and includes a circuit board, a vibrator and a UV sterilization lamp. The circuit board is electrically connected to a power source, and the vibrator is electrically connected to the circuit board. The UV sterilization lamp is located at the bottom surface of the mite-removing device and electrically connected to the circuit board. When the cleaner body is assembled with the mite-removing device, the mite-removing vacuum cleaner can perform mite-removing and dust-sucking functions both; when the cleaner body is disassembled from the mite-removing device, the cleaner body can perform the dust-sucking function independently. Therefore, the mite-removing vacuum cleaner of the present disclosure can provide the mite-removing and dust-sucking functions both, or provide the dust-sucking function independently.

10 Claims, 12 Drawing Sheets

MITE-REMOVING VACUUM CLEANER

BACKGROUND

1. Technical Field

The present disclosure relates to a vacuum cleaner, more particularly to an mite-removing vacuum cleaner.

2. Description of Related Art

Taiwan patent No. M424153 discloses a cleaner including a base frame, a beater member, a round brush, a UV sterilization lamp and a dust collection box. A handle is disposed at the rear part of the base frame and has a switch connected to a power line. The beater member is mounted to the base frame and exposed out of the bottom surface of the base frame, and includes a vibration motor and a beating sheet pivoted with the vibration motor. The vibration motor is configured to drive the beating sheet to quickly move up and down for beating. The round brush is disposed behind the beater member and exposed out of the bottom surface of the base frame, and includes a roller and bristles arranged on the roller in interval. A transmission mechanism is linked with the roller to drive the rotation of the roller. The UV sterilization lamp is disposed behind the round brush. The dust collection box is disposed behind the UV sterilization lamp and includes a base and two frames mounted inside the base. A fine filter and a micro-fine filter are respectively disposed on the two frames. While in use, the cleaner is placed flat on bedding or a planar object, the beater member is driven to beat the bedding or the planar object to lift bacteria, mites, dust and so on, and the round brush then sweeps the bedding or planar object for cleaning, and the UV sterilization lamp kills bacteria, mites and insect eggs. By means of the design that allergens including bacteria, mites and insect eggs are sucked into the dust collection box and filtered at the same time, the bedding and the planar object can be cleaned more conveniently and more effectively.

However, the beater member of the aforesaid cleaner is specially designed to remove mites of the bedding, so it is hard to use the cleaner installed with the beater member to suck dust on a place other than the bedding.

SUMMARY

A primary objective of the present disclosure is to provide an mite-removing vacuum cleaner capable of performing mite-removing and dust-sucking functions both, or performing the dust-sucking function independently.

According to the primary objective, the present disclosure provides an mite-removing vacuum cleaner comprising a cleaner body and a mite-removing device. The cleaner body is electrically connected to a power source and has a dust-sucking direction defined as the front thereof. The cleaner body has a handle, a first conductive member, a first vacuum port formed at the front thereof, a contacting surface formed at a lower edge of the first vacuum port and a fastening hole formed at a lateral side thereof. The mite-removing device is detachably assembled with the front section of the cleaner body and has a circuit board, a vibrator, a UV sterilization lamp and a fastening assembly. The circuit board is electrically connected to the power source, and the vibrator is electrically connected to the circuit board. The mite-removing device has a dust-sucking channel provided with an end formed as a second vacuum port and other end formed as a third vacuum port. The mite-removing device has at least one second conductive member corresponding to the first conductive member of the cleaner body, an opening formed at the bottom surface thereof and a receiving cavity formed by inwardly recessing from down to up at the opening. The UV sterilization lamp is disposed in the receiving cavity and electrically connected with the circuit board. A combination cavity is formed by inwardly recessing at the middle of a rear part of the mite-removing device and in communication with the second vacuum port. The sidewalls of the receiving cavity protrude into the combination cave to form a bearing surface corresponding to the contacting surface of the cleaner body. The fastening assembly is disposed correspondingly to the fastening hole of the cleaner body. When the mite-removing device is assembled with the cleaner body, the front section of the cleaner body is inserted into the combination cavity of the mite-removing device, the first vacuum port of the cleaner body is in communication with the second vacuum port of the mite-removing device, the contacting surface of the cleaner body is abutted against the bearing surface of the mite-removing device, the first conductive member of the cleaner body is in contact and electrically connected with the second conductive member of the mite-removing device, and the fastening assembly of the mite-removing device is fastened in the fastening hole of the cleaner body.

When the cleaner body and the mite-removing device are combined, the mite-removing vacuum cleaner of the present disclosure can perform mite-removing and dust-sucking functions both for the bedding; when the cleaner body is separated from the mite-removing device, the cleaner body can perform the dust-sucking function independently. Therefore, the mite-removing vacuum cleaner of the present disclosure can perform mite-removing and dust-sucking functions both, or perform the dust-sucking function independently.

In order to further understand the techniques, means and effects of the present disclosure, the following detailed descriptions and appended drawings are hereby referred, such that, through which, the purposes, features and aspects of the present disclosure can be thoroughly and concretely appreciated; however, the appended drawings are merely provided for reference and illustration, without any intention to be used for limiting the present disclosure.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DESCRIPTION OF THE EXEMPLARY EMBODIMENTS

Figure 1:
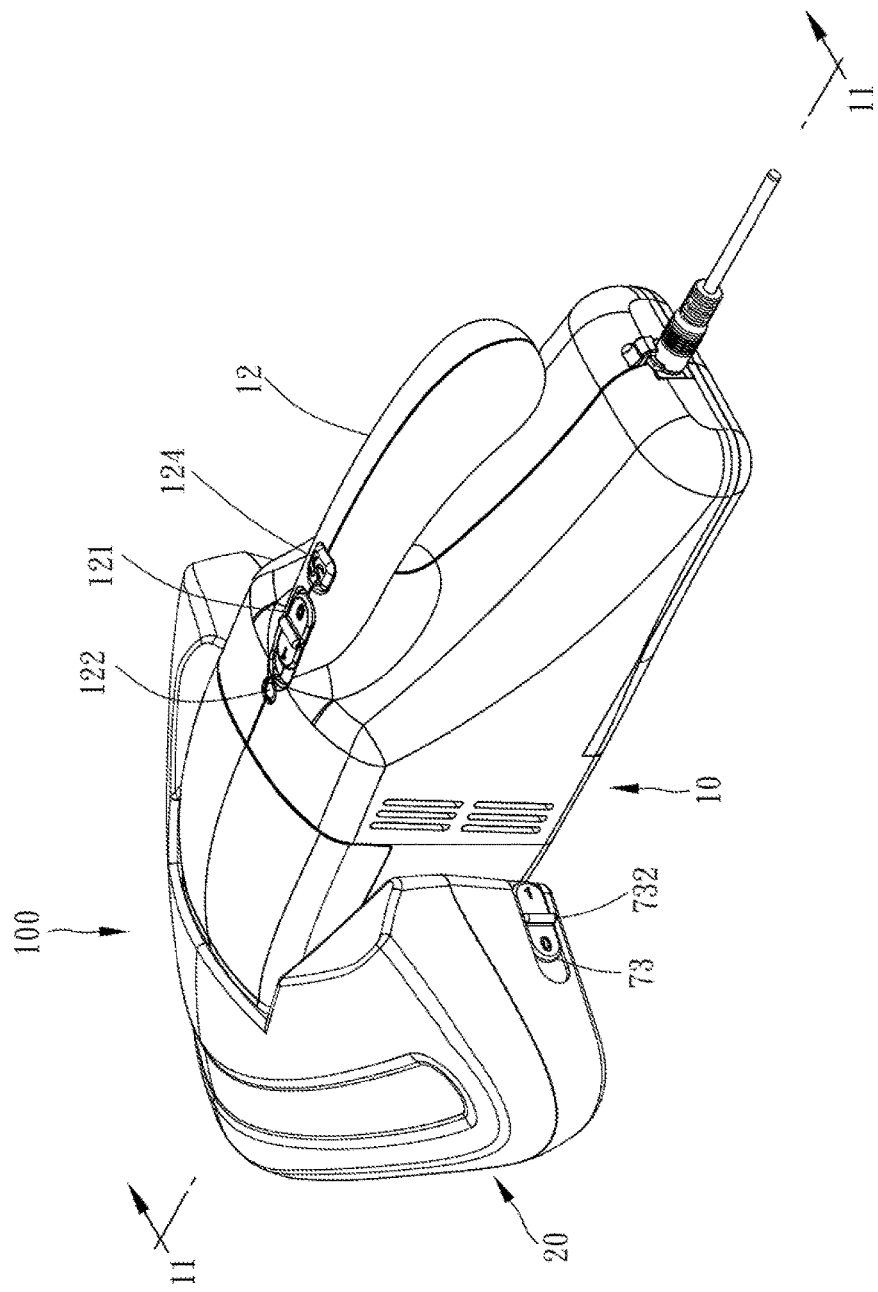
FIG. 1 is a perspective view of a first preferred embodiment of the present disclosure.

Reference will now be made in detail to the exemplary embodiments of the present disclosure, examples of which are illustrated in the accompanying drawings. Wherever possible, the same reference numbers are used in the drawings and the description to refer to the same or like parts.

Please refer to FIG. 1 through FIG. 11. An mite-removing vacuum cleaner 100 of a first preferred embodiment of the present disclosure comprises a cleaner body 10 and a mite-removing device 20.

Figure 2:
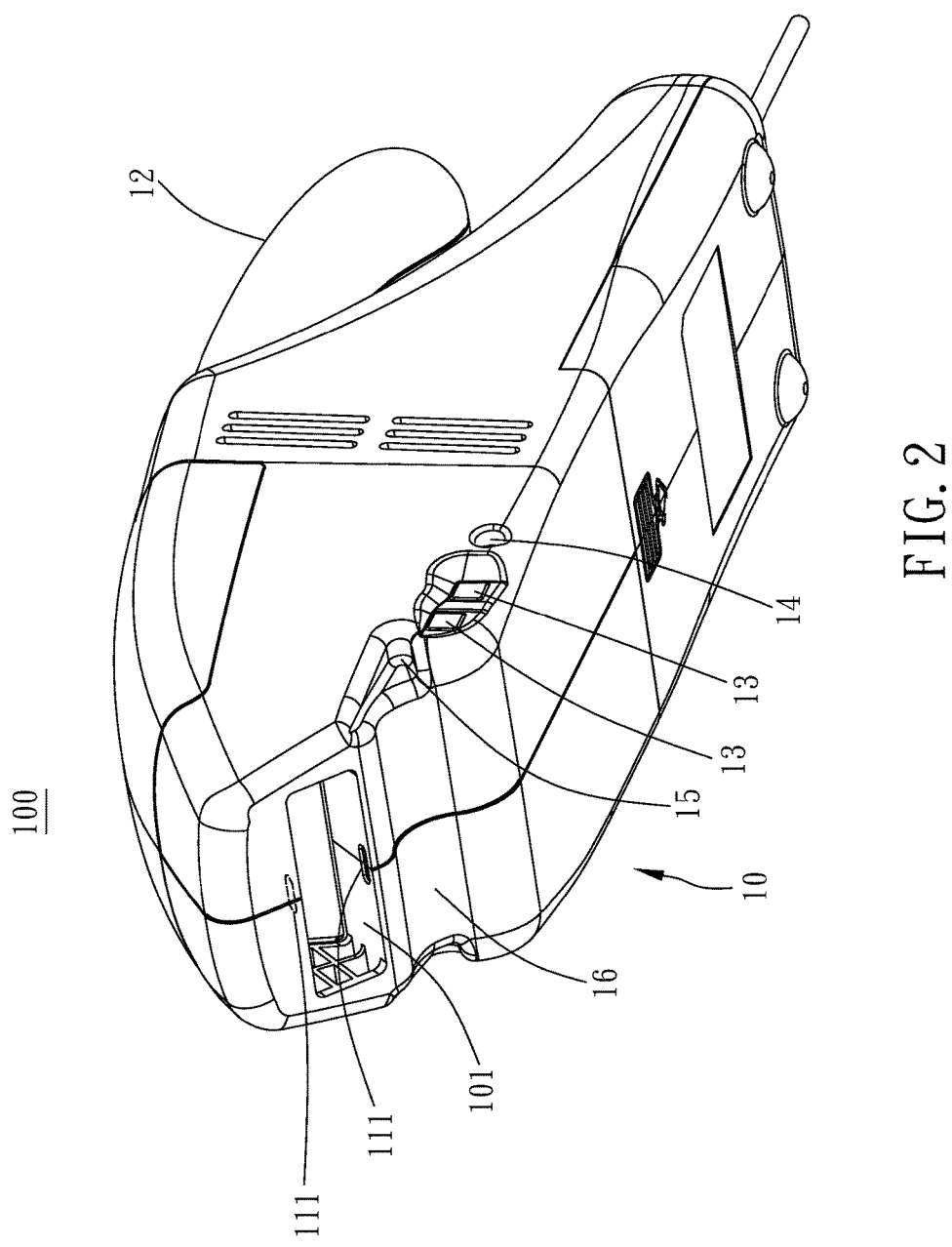
FIG. 2 is a perspective view of the cleaner body of the first preferred embodiment of the present disclosure.

The front of the cleaner body 10 is defined in a dust-sucking direction of the cleaner body 10, and the cleaner body 10 has a first vacuum port 101 at the front thereof and a handle 12. As shown in FIG. 2, the cleaner body 10 includes at least one first conductive member 13 and electrically connected with a power source (not shown in FIG. 2). As shown in FIG. 2, the cleaner body 10 has a contacting surface 16 formed at a lower edge of the first vacuum port 101 thereof, and the cleaner body 10 has a fastening hole 14. In first embodiment, the at least one first conductive member 13 is disposed at a lateral side of the cleaner body 10, and the fastening hole 14 of the cleaner body 10 is located behind the at least one first conductive member 13. The cleaner body 10 has pivot cavities 15 respectively located at the lateral sides thereof and ahead the at least one first conductive member 13. The contacting surface 16 of the cleaner body 10 is an arch-shaped and concave surface recessed inwardly at a lower edge of the first vacuum port 101.

In addition, as shown in FIG. 1, a power switch 121, an indicator light 122 and a suction up button 124 are disposed on the handle 12. The power switch 121 is configured to control turn-on/off of the power. When the power switch 121 is turned on, the indicator light 122 is lighted; when the power switch 121 is turned off, the indicator light 122 is darkened. The suction up button 124 is configured to control increasing of the suction of the cleaner body 10.

Figure 3:
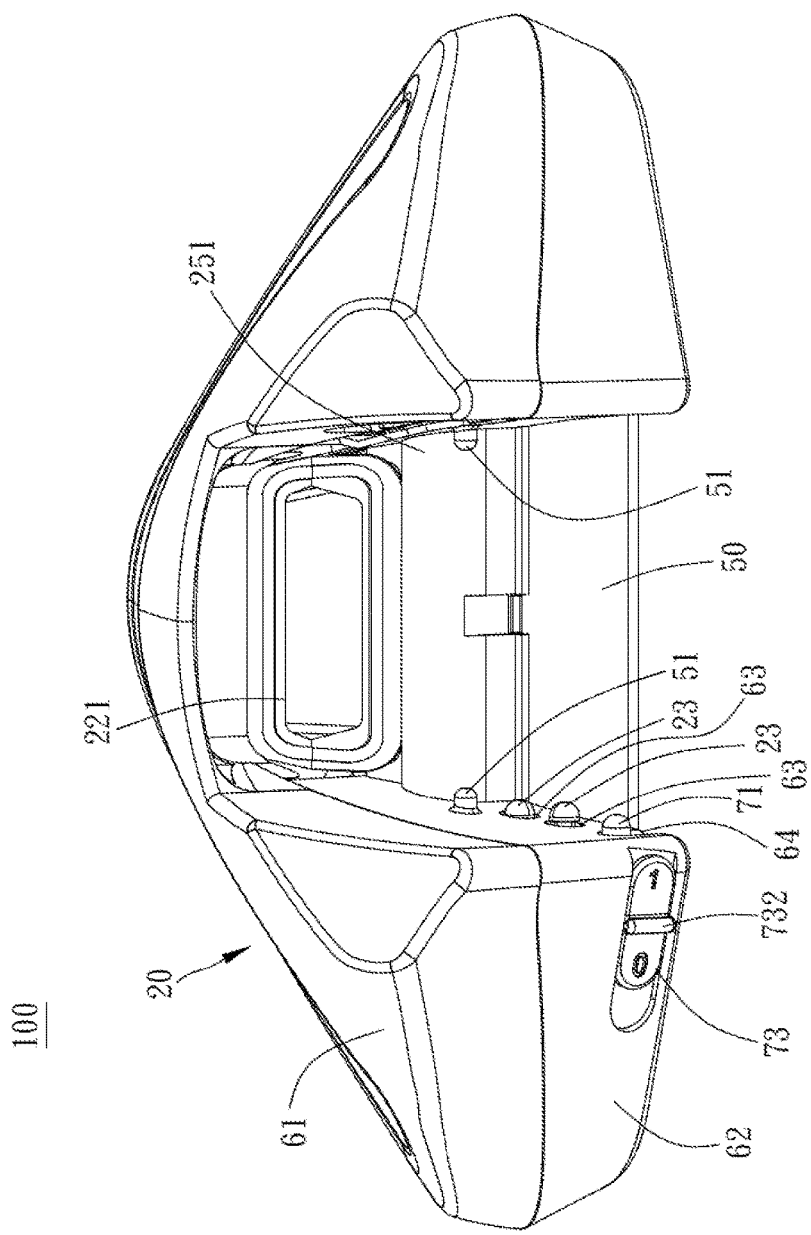
FIG. 3 is a perspective view of the mite-removing device of the first preferred embodiment of the present disclosure.
Figure 4:
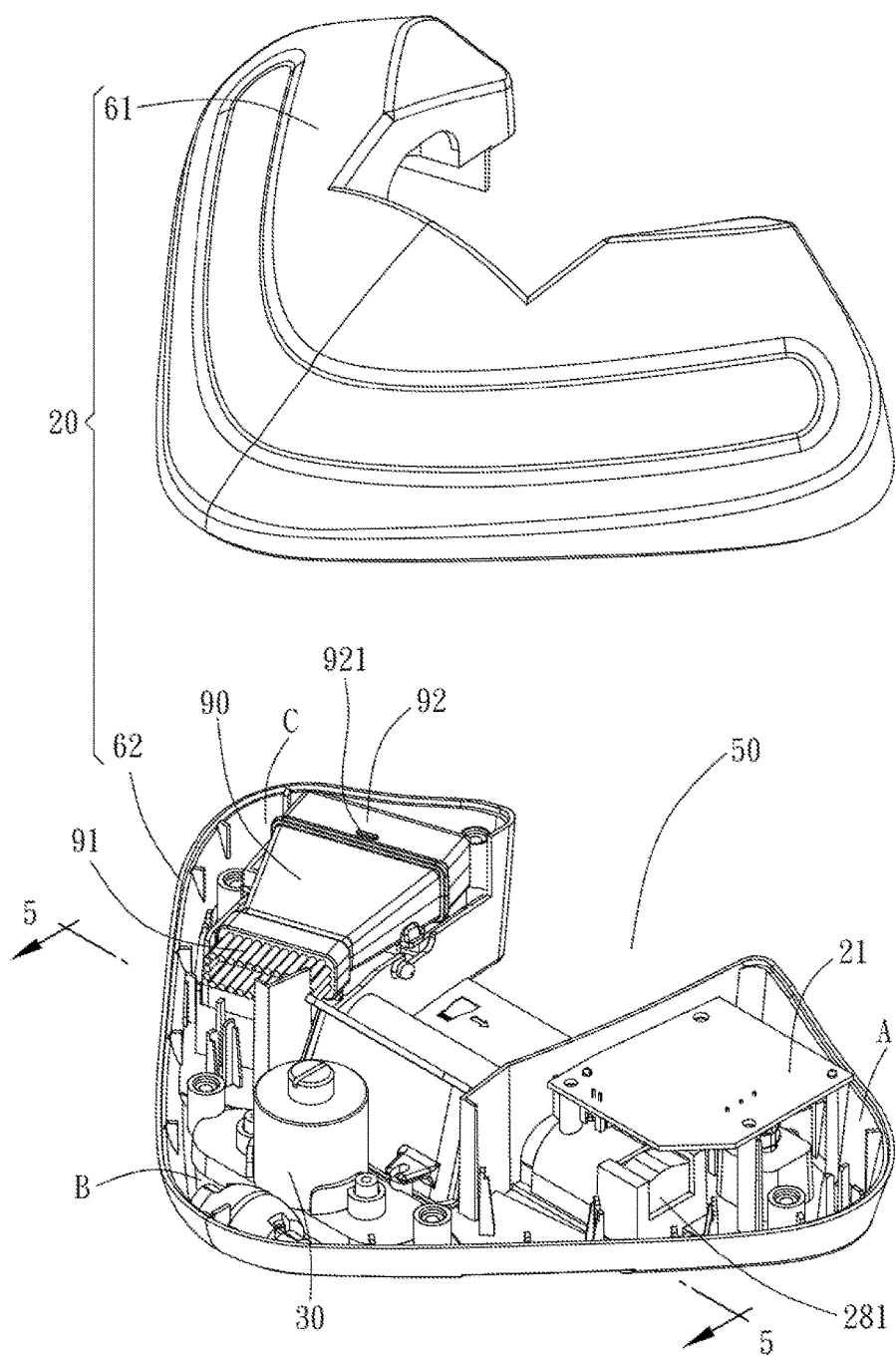
FIG. 4 is a perspective exploded view of the mite-removing device of the first preferred embodiment, illustrating that a top cover and a base are separated.
Figure 6:
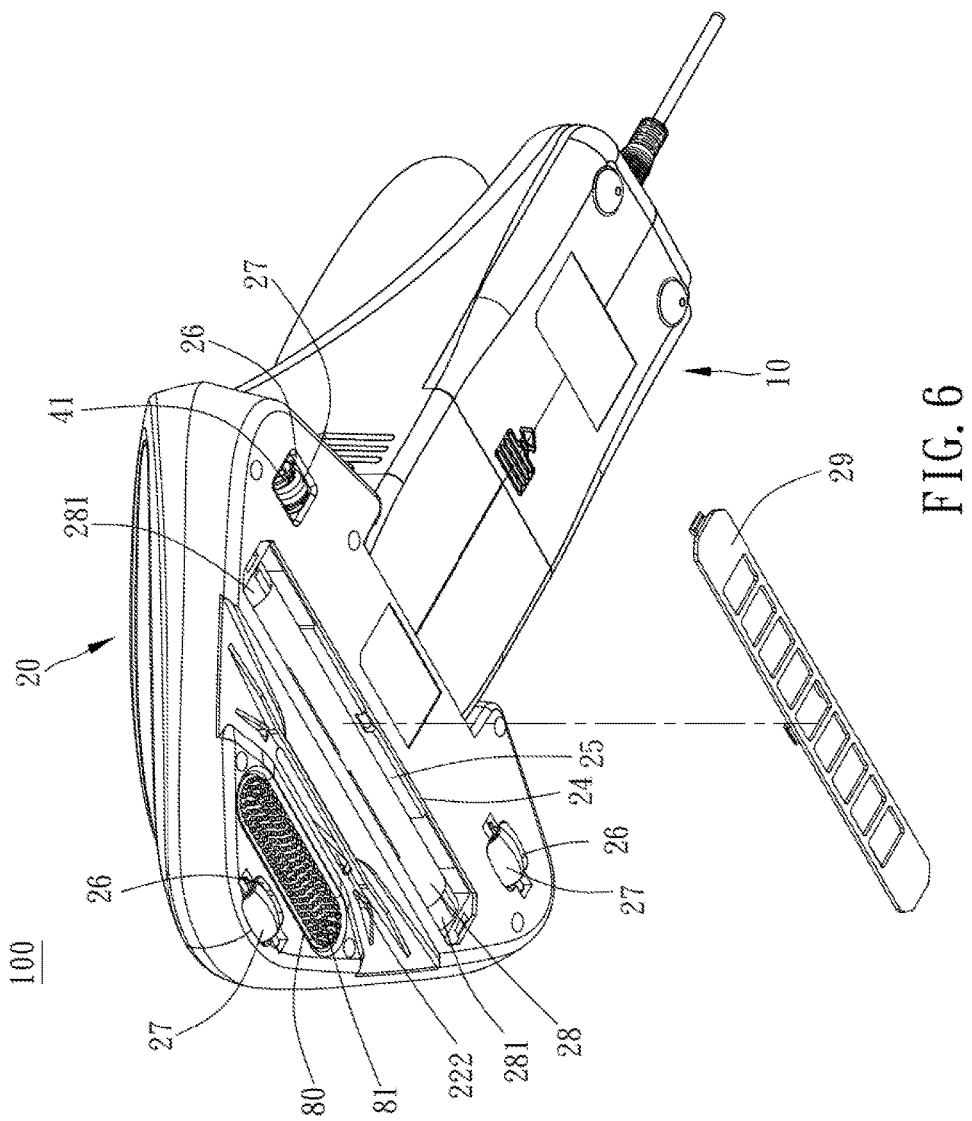
FIG. 6 is a bottom view of the first preferred embodiment of the present disclosure, illustrating that the transparent cover is separated from the mite-removing device.
Figure 7:
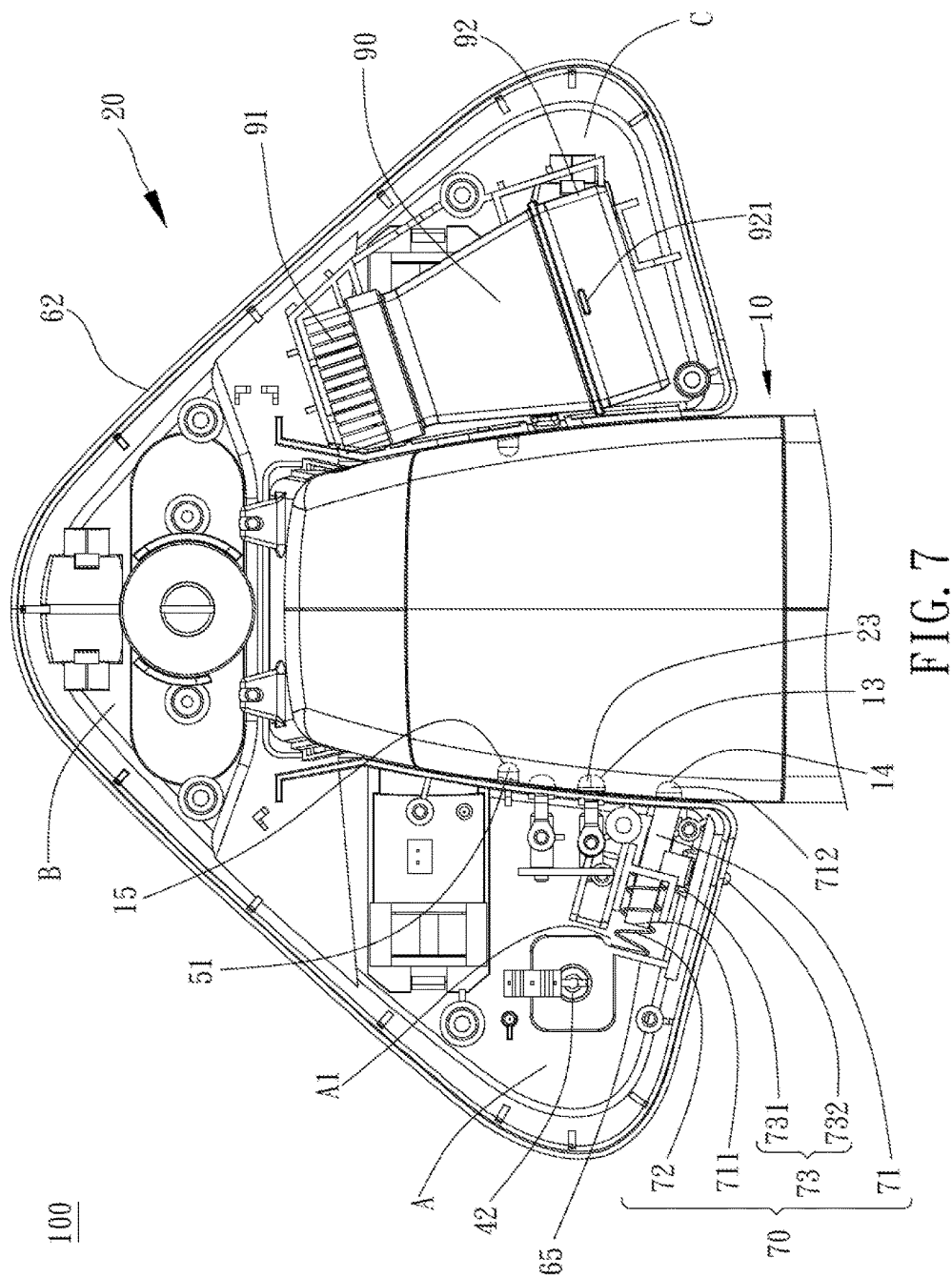
FIG. 7 is a top view of an internal structure of the first preferred embodiment of the present disclosure, illustrating that the fastening member is fastened in the fastening hole.
Figure 11:
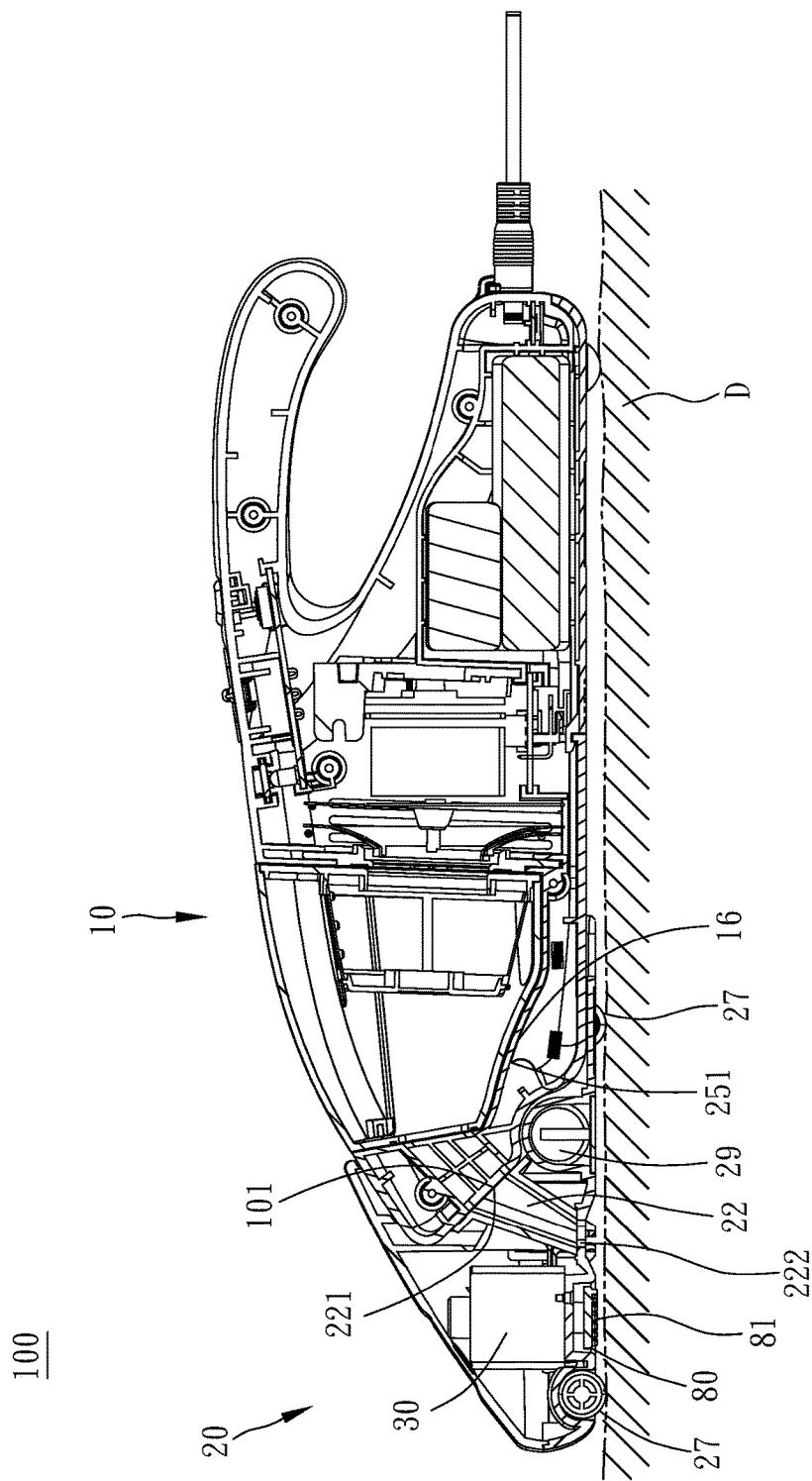
FIG. 11 is a cross-sectional view taken along line 11-11 of the FIG. 1, illustrating that the mite-removing vacuum cleaner is in a state of performing dust-sucking and mite-removing functions.

The mite-removing device 20 is detachably combined with the front section of the cleaner body 10, as shown in FIG. 1 through FIG. 3. The mite-removing device 20 includes a circuit board 21, a vibrator 30, a UV sterilization lamp 28 and a fastening assembly 70, as shown in FIGS. 4, 6 and 7. The circuit board 21 is electrically connected to the power source, and the vibrator 30 is electrically connected with the circuit board 21. The mite-removing device 20 has a dust-sucking channel 22 passed therethrough. As shown in FIG. 11, the dust-sucking channel 22 is formed with a second vacuum port 221 at an end thereof, and a third vacuum port 222 at an opposite end thereof. The mite-removing device 20 has at least one second conductive member 23 corresponding to the at least one first conductive member 13, as shown in FIGS. 2, 3 and 7. The at least one first conductive member 13 and the at least one second conductive member 23 are two in number as an example, respectively, in this embodiment. As shown in FIG. 6, the mite-removing device 20 has an opening 24 formed at a bottom surface thereof, and a receiving cavity 25 is formed by inwardly recessing from down to up at the opening 24. The UV sterilization lamp 28 is disposed in the receiving cavity 25 of the mite-removing device 20, as shown in FIG. 6, and electrically connected to the circuit board 21. The mite-removing device 20 has a combination cavity 50 formed by an inward recess at the middle of the rear part of the mite-removing device 20, and the combination cavity 50 and the second vacuum port 221 are in communication with each other. The sidewalls of the receiving cavity 25 protrude into the combination cavity 50 to form a bearing surface 251 corresponding to the contacting surface 16. The fastening assembly 70 is disposed correspondingly to the fastening hole 14 of the cleaner body 10, as shown in FIG. 2 and FIG. 3.

During assembly of the mite-removing device 20 and the cleaner body 10, the front section of the cleaner body 10 is combined with the mite-removing device 20, and the front section of the cleaner body 10 is positioned in the combination cavity 50, as shown in FIGS. 2, 3 and 7. The first vacuum port 101 is in communication with the second vacuum port 221, and the contacting surface 16 of the cleaner body 10 is abutted against the bearing surface 251 of the mite-removing device 20. Please refer to FIG. 11 together, the at least one first conductive member 13 is electrically connected with the at least one second conductive member 23, and the fastening assembly 70 is movably fastened in the fastening hole 14, as shown in FIG. 7.

In the first embodiment, a plurality of recessed parts 26 are formed on the bottom surface of the mite-removing device 20, as shown in FIG. 6, and a plurality of wheels 27 are respectively disposed in the recessed parts 26 of the mite-removing device 20. In addition, the mite-removing device 20 has two lamp sockets 281 disposed in the receiving cavity 25. The two lamp sockets 281 are electrically connected with the circuit board 21 and respectively combined with the two opposite ends of the UV sterilization lamp 28. In addition, the mite-removing device 20 has a transparent cover 29 for enclosing the opening 24 of the mite-removing device 20.

Figure 9:
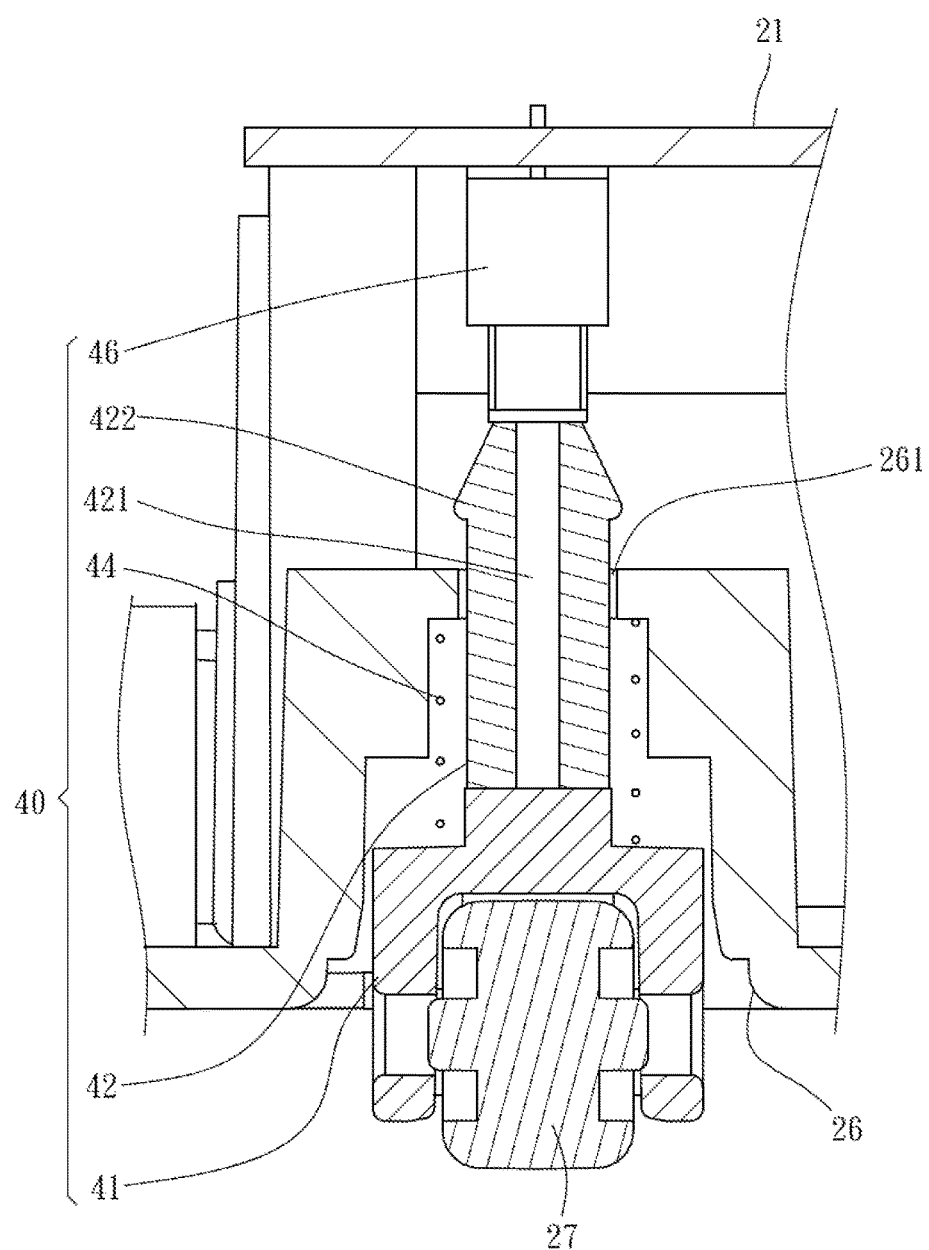
FIG. 9 is an enlarged sectional view of a part of the first preferred embodiment of the present disclosure, illustrating that the pushing rod is not in contact with the pressing switch.
Figure 10:
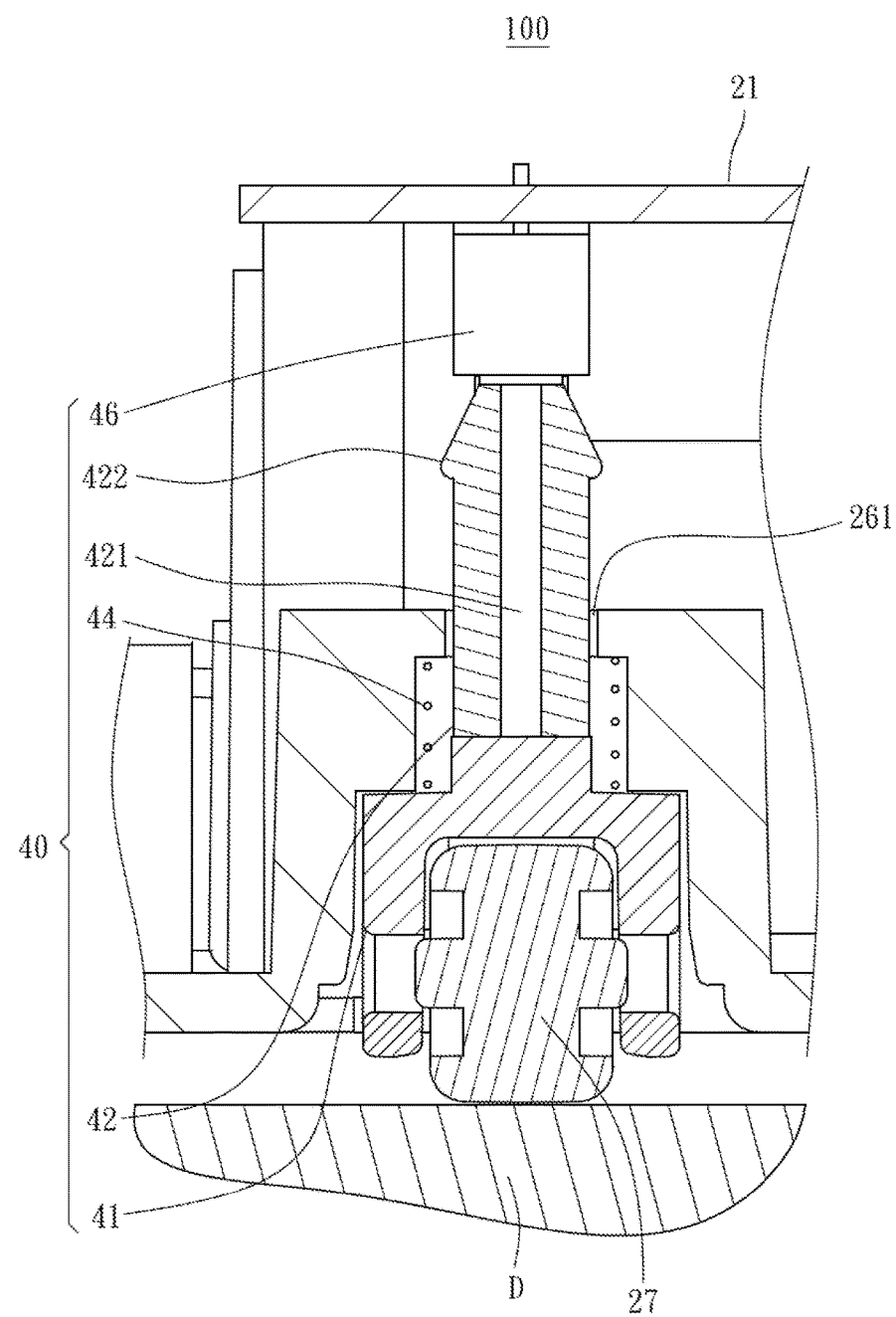
FIG. 10 is an enlarged sectional view of the part of the first preferred embodiment of the present disclosure, illustrating that the pushing rod is in contact with the pressing switch.

The mite-removing device 20 further has a pressing assembly 40, as shown in FIG. 9 and FIG. 10, and the recessed part 26 is formed with a hole 261 at a top wall thereof. The pressing assembly 40 is disposed in the recessed part 26 and under the circuit board 21 and includes a wheel frame 41, a pushing rod 42, a first spring 44 and a pressing switch 46. One of the wheels 27 is disposed in the wheel frame 41, and the wheel frame 41 extends upwardly to form the pushing rod 42. The pushing rod 42 is formed with a groove 421 cut therethrough and a larger-diameter part 422 located at an upper part of the pushing rod 42. A diameter of the larger-diameter part 422 of the pushing rod 42 is larger than a diameter of the hole 261. Because of the groove 421, the larger-diameter part 422 of the pushing rod 42 can be elastically compressed to pass through the hole 261, so as to abut against the top wall of the recessed part 26 and positioned above the hole 261. The first spring 44 is sleeved on the pushing rod 42 and constrained between the top wall of the recessed part 26 and an upper surface of the wheel frame 41. The top end of the pushing rod 42 is in contact with the pressing switch 46 which is electrically connected to the circuit board 21.

In addition, the mite-removing device 20 has a top cover 61 and a base 62, as shown in FIGS. 3 and 4. The top cover 61 is covered the base 62 correspondingly. A first chamber A is formed between the top cover 61 and a hollow part at a side of the base 62. A wall between the base 62 and the combination cavity 50 is formed with at least one first aperture 63 and a second aperture 64. In this embodiment, the at least one first aperture 63 is two in number as an example, and the second aperture 64 is located behind the two first apertures 63. The two second conductive members 23 are disposed in the first chamber A of the base 62 and partially pass through the two first apertures 63, respectively. The base 62 has two pivot pins 51 protruding therefrom toward the combination cavity 50 and disposed correspondingly to the two pivot cavities 15 and located ahead the two second conductive members 23. In addition, the circuit board 21 is disposed inside the first chamber A, as shown in FIG. 4.

Figure 5:
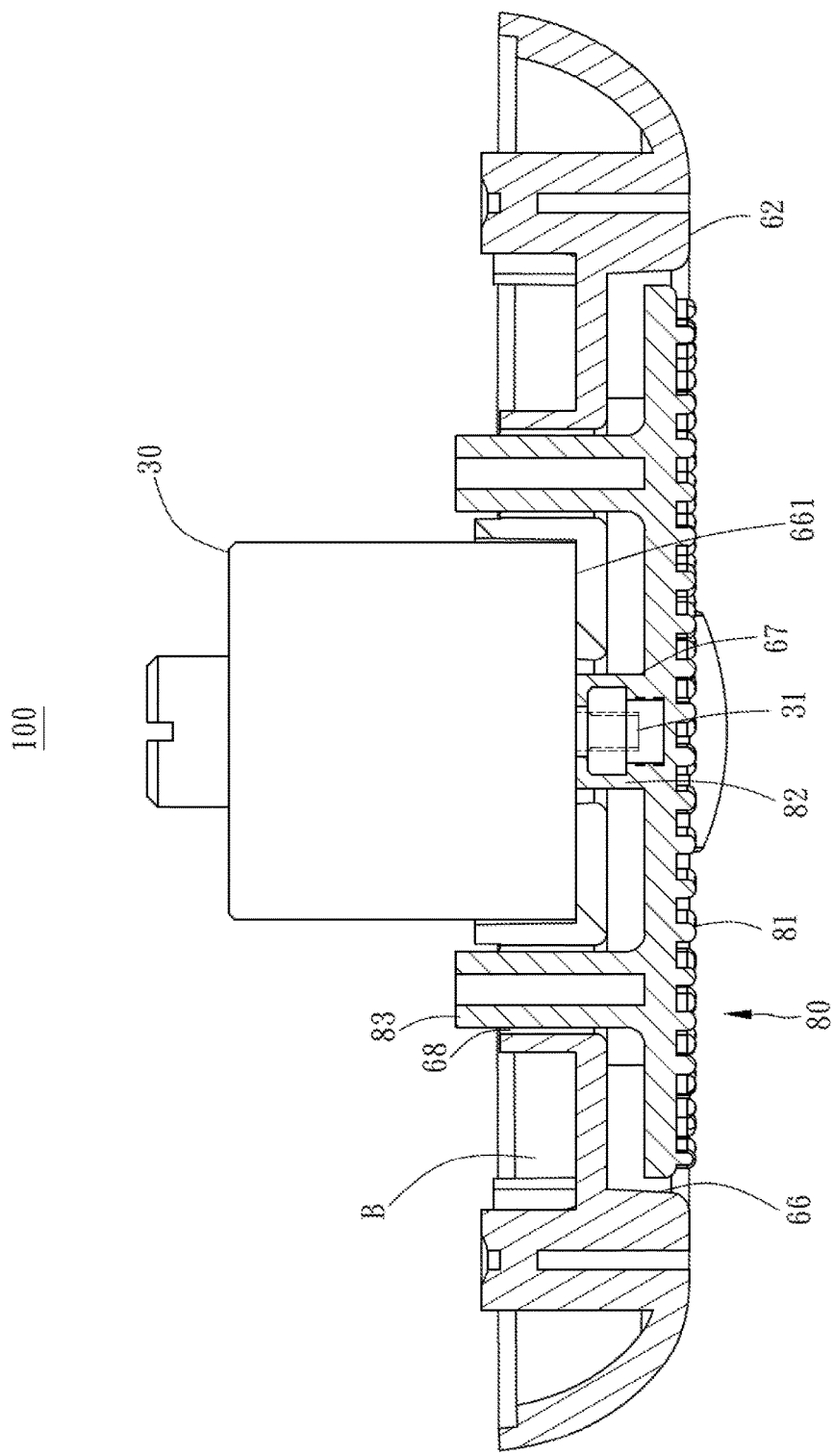
FIG. 5 is a cross-sectional view taken along line 5-5 of the FIG. 4, illustrating that the vibrator and the first brush are combined with the base.

Please refer to FIG. 4 through FIG. 6. A second chamber B is formed between the top cover 61 and a hollow part at a front section of the base 62. The base 62 has a cavity 66 inwardly recessed from the bottom to top thereof, and the cavity 66 is located ahead the third vacuum port 222. The sidewalls of the cavity 66 protrude into the second chamber B to form a combination surface 661, and the sidewalls of the cavity 66 are provided with a combination hole 67 and two through holes 68. In addition, as shown in FIG. 4, a third chamber C is formed between the top cover 61 and a hollow part at opposite side of the base 62, and a second brush 90 is disposed in the third chamber C.

Please refer to FIGS. 5 and 6. The vibrator 30 is disposed on the combination surface 661 and includes a combination block 31 passing through the combination hole 67. In addition, a first brush 80 is disposed in the cavity 66 and has a first brush part 81 at end thereof, and a connecting part 82 and two first protrusions 83 at an opposite end thereof. The connecting part 82 and the two first protrusions 83 are respectively inserted into the combination hole 67 and the two through holes 68, and the connecting part 82 of the first brush 80 is combined with the combination block 31 of the vibrator 30.

Figure 8:
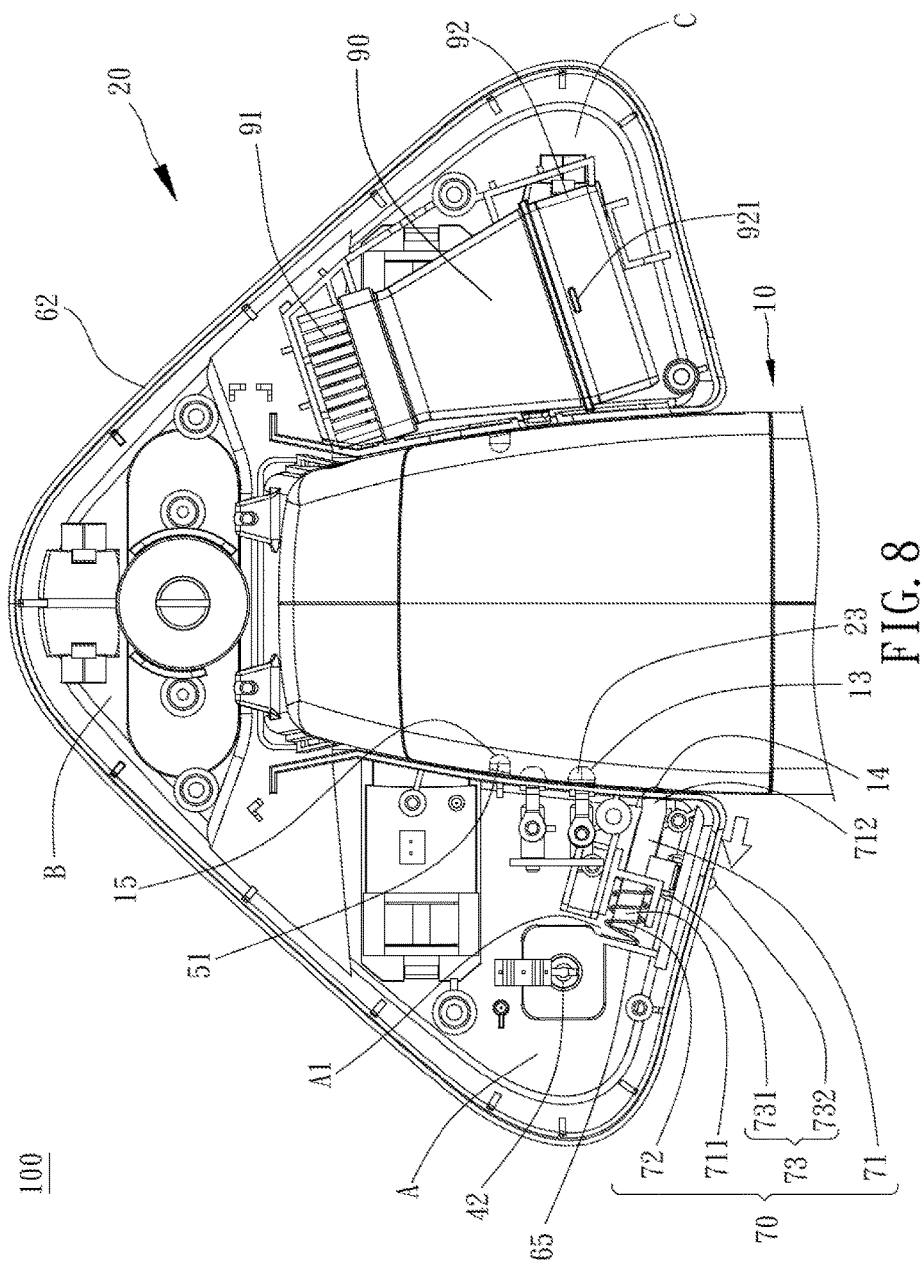
FIG. 8 is a top view of the internal structure of the first preferred embodiment of the present disclosure, illustrating that the fastening member is not fastened in the fastening hole.

Please refer to FIGS. 7 and 8. A divider 65 is formed in the first chamber A of the mite-removing device 20 and a space A1 is formed by surrounding between the divider 65 and a backside wall of the first chamber A. The fastening assembly 70 is located in the space A1 and includes a fastening member 71, a second spring 72 and a pushing member 73. The fastening member 71 has an end formed with a mounting part 711 and an opposite end formed with a fastening part 712. The second spring 72 has an end mounted on and abutted against the mounting part 711, and an opposite end abutted against the divider 65. While being pressed by the mounting part 711, the second spring 72 is compressed to store an elastic force. The fastening part 712 of the fastening member 71 is movably inserted into the second aperture 64 to movably fasten in the fastening hole 14. The base 62 has a through-opening (not shown in Figs) formed at the back sidewall of the first chamber A. The pushing member 73 has an end extending to form a linking part 731 and an opposite end formed with a pushing part 732. The linking part 731 of the pushing member 73 is inserted into the through-opening to connect with the fastening member 71.

In the first embodiment, the vibrator 30 includes an electromagnet (not shown in Figs) and a spring (not shown in Figs). The vibrator 30 is a well-known technology, so the electromagnet and the spring are just taken as examples for the vibrator 30, but the present disclosure is not limited thereto.

The above description illustrates the structure of the first preferred embodiment of the present disclosure, and the operation of the first preferred embodiment of the present disclosure is described blow.

The vacuum cleaner 100 of the first embodiment can be operated in two states, one is mite-removing state and the other is dust-removing state.

Please refer to FIG. 1 through FIG. 11. When the vacuum cleaner 100 is operated in mite-removing state, the front section of the cleaner body 10 is inserted into the combination cavity 50 of the mite-removing device 20, as shown in FIG. 1 through FIG. 3 and, in the meantime, the first vacuum port 101 of the cleaner body 10 is aligned with the second vacuum port 221 of the mite-removing device 20 and they are in communication with each other, as shown in FIG. 11, the contacting surface 16 of the cleaner body 10 is abutted against the bearing surface 251 of the mite-removing device 20, the two pivot pins 51 of the mite-removing device 20 are pivoted with the two pivot cavities 15 of the cleaner body 10. Please further refer to the FIG. 7. The two first conductive members 13 of the cleaner body 10 are in contact and electrically connected with the two second conductive members 23 of the mite-removing device 20, the fastening part 712 of the fastening member 71 of the mite-removing device 20 is fastened in the fastening hole 14 of the cleaner body 10. After the cleaner body 10 is combined with the mite-removing device 20, they are placed flat on a bedding D, such as bedquilt, bed sheet, bed cover and so on. Please refer to FIG. 10, the wheel 27 of the pressing assembly 40 presses against the bedding D, so that the wheel frame 41 is moved upwardly to compress the first spring 44, the top end of the pushing rod 42 touches the pressing switch 46 to turn on the UV sterilization lamp 28. At the same time, the vibrator 30 generates vibration to enable left and right wing parts of the mite-removing device 20 to beat the bedding D by turns, so that the bacteria, mites, insect egg and dust of the bedding D are lifted, the first brush part 81 of the first brush 80 can sweep and clean the bedding D, and the UV sterilization lamp 28 can kill the lifted bacteria, mites and insect egg. Through the third vacuum port 222, the dust-sucking channel 22 and the second vacuum port 221 of the mite-removing device 20, and the first vacuum port 101 of the cleaner body 10, the dissolved and killed bacteria, mites, and insect eggs are completely sucked into the cleaner body 10, thereby achieving the effect of removing dust and mites on the bedding D or other planar objects (not shown in drawings).

Please refer to FIG. 2 and FIG. 8. In dust-sucking state of the vacuum cleaner 100, the pushing part 732 of the pushing member 73 is used to drive the fastening member 71 to compress the second spring 72, to enable the fastening part 712 of the fastening member 71 to escape from the fastening hole 14, as shown in FIG. 8, so that the cleaner body 10 is separated from the mite-removing device 20. Next, as shown in FIG. 2, the cleaner body 10 can be independently used to suck dust without limitation in cleaning the bedding D or other planar objects only due to the constraint caused by the mite-removing device 20.

As described above, when the cleaner body 10 and the mite-removing device 20 are combined, the mite-removing vacuum cleaner 100 of the present disclosure can be operated to suck duct and remove mites from bedding D; alternatively, when the cleaner body 10 and the mite-removing device 20 are separated from each other, the cleaner body 10 can be used to suck dust independently. Therefore, the mite-removing vacuum cleaner 100 can perform mite-removing and dust-sucking functions both, or perform the general dust-sucking function independently.

In the first preferred embodiment, the at least one first conductive member 13, the at least one second conductive member 23 and the at least one first aperture 63 are two in number, respectively, but these are just examples and the present disclosure is not limited thereto. In practice, the vacuum cleaner 100 can has single first conductive member 13, single second conductive member 23 and single first aperture 63, and their implementation can refer to the first preferred embodiment, so not shown in drawings.

Figure 12:
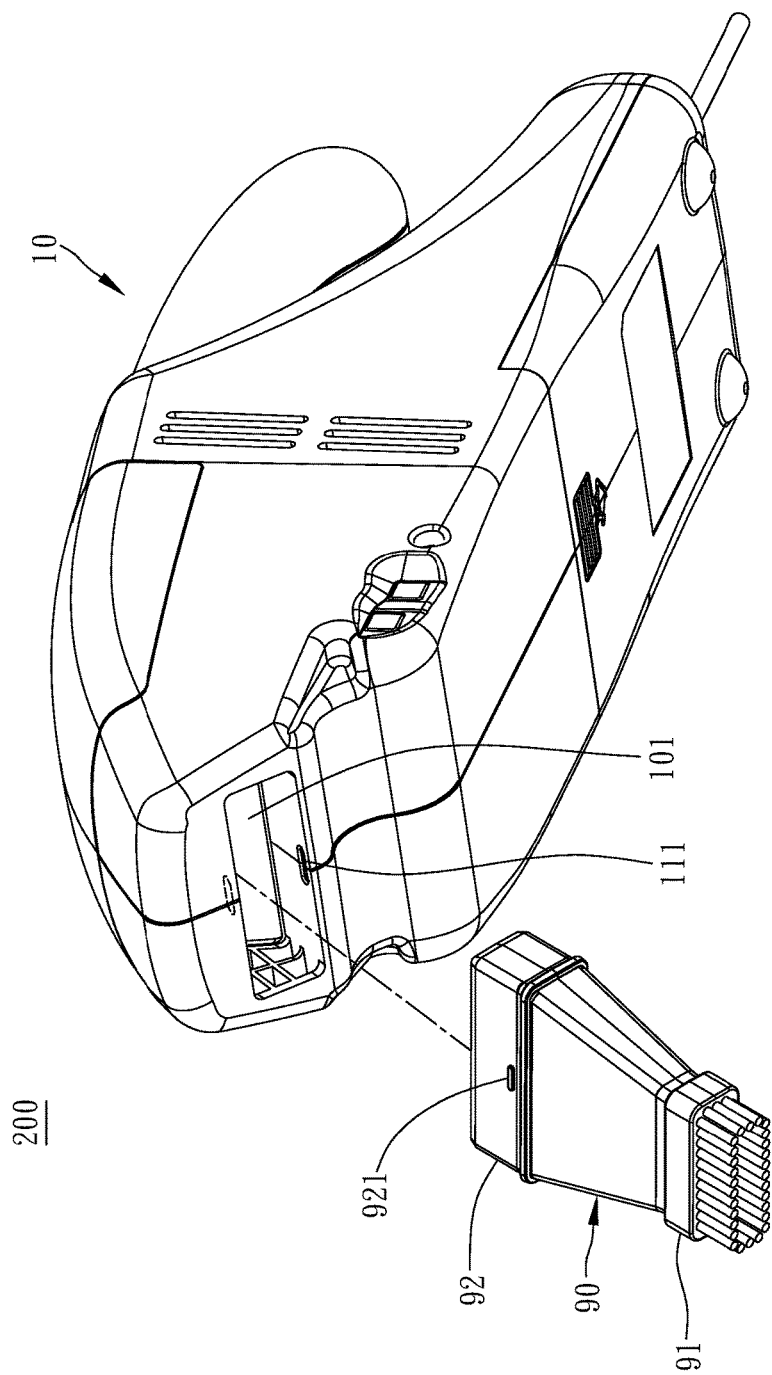
FIG. 12 is a perspective view of the cleaner body and the second brush of a second preferred embodiment of the present disclosure.

Please refer to FIG. 12. A second preferred embodiment of the present disclosure provides an mite-removing vacuum cleaner 200 similar to the first embodiment, and the difference between the second preferred embodiment and the first preferred embodiment is described below.

The sidewalls of the first vacuum port 101 are formed with at least one fastening slot 111, and the second embodiment further includes a second brush 90 which has a second brush part 91 and a second protrusion 92. The protrusion 92 is formed with at least one stop block 921 corresponding to the at least one fastening slot 111. In the second embodiment, the at least one fastening slot 111 and the at least one stop block 921 are two in number, respectively, for example.

In operation, the cleaner body 10 is mounted with the second brush 90 to perform general dust-sucking function.

As described above, in the second preferred embodiment, the at least one fastening slot 111 and the at least one stop block 921 are two in number, respectively, but the present disclosure is not limited thereto. In practice, the fastening slot 111 and the stop block 921 can be single, respectively, and their implementation can refer to the second preferred embodiment, so not shown in drawings.

Other structures of the second preferred embodiment of the present disclosure are the same as that of the first preferred embodiment, so their detail description is omitted.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:

1. An mite-removing vacuum cleaner comprising:
   a cleaner body having a dust-sucking direction defined as the front thereof, wherein the cleaner body is electrically connected with a power source and has a first vacuum port formed at the front thereof, a handle, at least one first conductive member, a contacting surface formed at a lower edge of the first vacuum port thereof, and a fastening hole formed at a lateral side thereof; and
   a mite-removing device detachably assembled with a front section of the cleaner body and having a circuit board electrically connected with the power source, a vibrator electrically connected with the circuit board, a UV sterilization lamp and a fastening assembly; wherein the mite-removing device has a dust-sucking channel provided with an end formed as a second vacuum port and other end formed as a third vacuum port, at least one second conductive member corresponding to the at least one first conductive member of the cleaner body, an opening formed at a bottom surface thereof, a receiving cavity formed by inwardly recessing from down to up at the opening, a combination cavity formed by inwardly recessing at a middle of a rear part thereof and in communication with the second vacuum port, and a bearing surface formed by the sidewalls of the receiving cavity protruding into the combination cavity and corresponding to the contacting surface of the cleaner body, the UV sterilization lamp disposed in the receiving cavity and electrically connected with the circuit board and the fastening assembly disposed correspondingly to the fastening hole of the cleaner body;
   wherein when the mite-removing device is combined with the cleaner body, the front section of the cleaner body is inserted into the combination cavity of the mite-removing device, the first vacuum port of the cleaner body is in communication with the second vacuum port of the mite-removing device, the contacting surface of the cleaner body is abutted against the bearing surface of the mite-removing device, the at least one first conductive member of the cleaner body is in contact and electrically connected with the at least one second conductive member of the mite-removing device, and the fastening assembly of the mite-removing device is movably fastened with the fastening hole of the cleaner body.

2. The mite-removing vacuum cleaner according to claim 1, wherein a plurality of recessed parts are formed by inwardly recessing at the bottom surface of the mite-removing device, and a plurality of wheels are respectively disposed in the plurality of recessed parts of the mite-removing device.

3. The mite-removing vacuum cleaner according to claim 2, wherein the mite-removing device has two lamp sockets disposed in the receiving cavity and respectively connected with two opposite ends of the UV sterilization lamp and electrically connected with the circuit board.

4. The mite-removing vacuum cleaner according to claim 3, wherein a hole is formed on a top wall of one of the recessed parts; the mite-removing device includes a pressing assembly disposed in one of the recessed parts and located under the circuit board and having a wheel frame, a pushing rod, a first spring and a pressing switch, wherein one of the wheels is disposed in the wheel frame which extends upwardly to form the pushing rod, and the pushing rod is provided with a groove cut therethrough and a larger-diameter part a top thereof passing through the hole to abut against the top wall of the recessed part and position over the hole, and the first spring is sleeved on the pushing rod and constrained between an inner edge of the top wall of the recessed part and an upper surface of the wheel frame; the pushing rod has a top end in contact and electrically connected with the pressing switch that is electrically connected with the circuit board.

5. The mite-removing vacuum cleaner according to claim 1, wherein the at least one first conductive member is disposed on the lateral side of the cleaner body, and the fastening hole of the cleaner body is located behind the at least first conductive member; the cleaner body has two pivot cavities respectively disposed at two opposite sides thereof and located ahead the at least one first conductive member, and the contacting surface of the cleaner body is an arch-shaped and concave surface formed at lower edge of the first vacuum port; wherein the mite-removing device has a top cover and a base covered by the top cover; a first chamber is formed between the top cover and a hollow part at a side of the base; at least one first aperture and second aperture are formed on the wall between the base and the combination cavity, and the at least first aperture is located ahead the second aperture; the at least one second conductive member is disposed in the first chamber of the base, and a part of the at least one second conductive member passes through the at least one first aperture; the base has two pivot pins protruding toward the combination cavity and located corresponding to the two pivot cavities and located ahead the at least one second conductive member; the circuit board is disposed in the first chamber.

6. The mite-removing vacuum cleaner according to claim 5, wherein a divider is formed in the first chamber of the mite-removing device, and a space is formed by surrounding the divider and a backside wall of the first chamber; the fastening assembly is disposed in the space and includes a fastening member, a second spring and a pushing member, wherein the fastening member has an end formed with a mounting part and other end formed with a fastening part, and the second spring has an end sleeved on the mounting part of the fastening member and abutted against the mounting part of the fastening member, and an opposite end abutted against the divider, such that the second spring is compressed by the mounting part of the fastening member to store an elastic force; the fastening part of the fastening member is movably inserted into the second aperture and movably fastened in the fastening hole; the base has a through-opening formed at the backside wall of the first chamber, and the pushing member has an end extending to form a linking part inserted through the through-opening and connected with the fastening member and the other end formed with a pushing part.

7. The mite-removing vacuum cleaner according to claim 5, wherein a second chamber is formed between a front hollow part of the base and the top cover, and the base has a cavity formed by inwardly recessing from down to up and located ahead the third vacuum port and provided with sidewalls thereof protruding into the second chamber to form a combination surface, and a combination hole and two through holes are formed on the sidewalls of the cavity;
    wherein the vibrator is disposed on the combination surface and has a combination block which is inserted through the combination hole;
    wherein the mite-removing vacuum cleaner further comprises a first brush which has an end formed with a first brush part and other end formed with a connecting part and two first protrusions; the first brush is disposed on the bottom surface of the base and located in the cavity, and the connecting part and the two first protrusions are respectively inserted into the combination hole and the two through holes, and the connecting part of the first brush is combined with the combination block of the vibrator.

8. The mite-removing vacuum cleaner according to claim 5, wherein a third chamber is formed between the top cover and a hollow part at other side of base; the mite-removing vacuum cleaner further comprises a second brush disposed in the third chamber.

9. The mite-removing vacuum cleaner according to claim 1, wherein a wall of the first vacuum port is formed with at least one fastening slot; the mite-removing vacuum cleaner further comprises a second brush which has a second brush part and a second protrusion provided with at least one stop block detachably engaged with the at least one fastening slot.

10. The mite-removing vacuum cleaner according to claim 1, wherein the mite-removing device has a transparent cover configured to cover the opening of the mite-removing device.

* * * * *